United States Patent
Parker et al.

(10) Patent No.: US 6,326,196 B1
(45) Date of Patent: Dec. 4, 2001

(54) NITRATE REDUCTASE-TRANSFECTED HELA CELLS FOR CANCER AND MICROWAVE BIOEFFECTS RESEARCH

(75) Inventors: Jill E. Parker, Floresville; Johnathan L. Kiel, Universal City, both of TX (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/766,017

(22) Filed: Jan. 22, 2001

(51) Int. Cl.$^7$ .................................................. C12N 5/08
(52) U.S. Cl. ........................................ 435/367; 435/320.1
(58) Field of Search ................................ 435/367, 320.1

(56) References Cited

U.S. PATENT DOCUMENTS

| | | |
|---|---|---|
| 5,003,050 | 3/1991 | Kiel et al. . |
| 5,464,768 | 11/1995 | Kiel et al. . |
| 5,856,108 | 1/1999 | Kiel et al. . |
| 6,013,520 | 1/2000 | Parker et al. . |

*Primary Examiner*—James Ketter
(74) *Attorney, Agent, or Firm*—Charles E. Bricker; Thomas L. Kundert

(57) ABSTRACT

The cell line HeLa is transformed with the chromosomal insertion of the plasmid pSV$_2$neoNR10$_1$, ATCC No. 69617. The transformed cells, HeLaNR1, produce diazoluminomelanin (DALM) intra cellularly when provided with nitrate, luminol and 3-amino-L-tyrosine•HC1 (3AT). The modified cells can be used to study mechanisms for radiofrequency and light radiation interactions with carcinoma of the cervix. The effects of drugs, hormones, and cytokines that affect the expression of nitric oxide synthase and its activity can also be studied to understand the effects of these materials on cervix cells.

1 Claim, 1 Drawing Sheet

NITRATE REDUCTASE-TRANSFECTED HELA CELLS FOR CANCER AND MICROWAVE BIOEFFECTS RESEARCH

RIGHTS OF THE GOVERNMENT

The invention described herein may be manufactured and used by or for the Government of the United States for all governmental purposes without the payment of any royalty.

BACKGROUND OF THE INVENTION

The present invention relates to cervical carcinoma cells (HeLa) modified with a nitrate reductase gene fragment.

U.S. Pat. No. 5,003,050, "Diazoluminomelanin and a method for preparing same", issued Mar. 26, 1991 to Kiel et al, describes a polymeric water-soluble luminescent compound having repeating units comprising diazo-linked luminol and hydroxyindole and referred to as diazoluminomelanin (DALM). DALM can be used for chemiluminescent immunoassays for biological and chemical agents; in radiofrequency and ionizing radiation dosimeters; and for RNA/DNA hybridization assays for viruses and genetic detection.

It was found that DALM can be biosynthesized by culturing a microorganism containing nitrate reductase in a medium containing nitrate, 3-aminog-L-tyrosine (3-AT) and luminol under suitable metabolic conditions. U.S. Pat. No. 5,856,108, "Biosynthesis of diazomelanin and diazoluminomelanin and methods thereof", issued Jan. 5, 1999 to Kiel et al.

U.S. Pat. No. 5,464,768, "Enhanced nitrite production in transfected murine cells", issued Nov. 7, 1995 to Kiel et al, describes mammalian cells line capable of enhanced nitrite production prepared by transfecting a murine macrophage or murine thymoma with barley nitrate reductase gene (NR). The cell lines can be used for the production of diazomelanin (DM) and diazoluminomelanin (DALM). Production of DM is achieved by culturing the cells in a medium containing a nitrate source and 3-amino-L-tyrosine under suitable metabolic conditions.

We then successfully modified EMT-6 cells (spontaneous Balb/c mammary adenocarcinoma cell line) with the chromosomal insertion of the plasmid $pSV_2neoNR10_1$, ATCC No. 69617. U.S. Pat. No. 6,013,520, "Breast tumor cells for study of nonionizing radiation effects", issued Jan. 11, 2000 to Parker et al. The transformed cells, EMT-6/$pSV_2neoNR10_1$, produce diazoluminomelanin (DALM) intra cellularly when provided with nitrate, luminol and 3-amino-L-tyrosine•HCl (3AT). The modified cells can be used to study mechanisms for radiofrequency and light radiation interactions with breast tumor cells in vitro and in mice. The effects of drugs, hormones, and cytokines that affect the expression of nitric oxide synthase and its activity can also be studied to understand the effects of these materials on breast tumor cells.

Cervical cancer is one of the most common malignancies in women and remains a significant public health problem throughout the world. In the United States alone, invasive cervical cancer accounts for approximately 19% of all gynecological cancers. In 1996, it is estimated that there will be 14,700 newly diagnosed cases and 4900 deaths attributed to this disease. In many developing countries, where mass screening programs are not widely available, the clinical problem is more serious. Worldwide, the number of new cases is estimated to be 471,000 with a 4 year survival rate of 40%.

Previous attempts to transfect human cells with a functional nitrate reductase gene have not, until now, been successful. We have now transfected a human cell line, HeLa, with a barley nitrate reductase gene fragment. This cell line can be traced back to a woman named Henrietta Lacks, who died of cervical cancer in the early 1950s.

Accordingly, it is an object of the present invention to provide a human carcinoma cell modified with a nitrate reductase gene fragment.

Other objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

In accordance with the present invention there are provided HeLa cells transformed with the chromosomal insertion of the plasmid $pSV_2neoNR10_1$, ATCC No. 69617. The transformed cells, hereinafter referred to as HeLaNR1, produce diazoluminomelanin (DALM) intra cellularly when provided with nitrate, luminol and 3-amino-L-tyrosine•HCl (3AT).

DETAILED DESCRIPTION OF THE INVENTION

Figure 1:
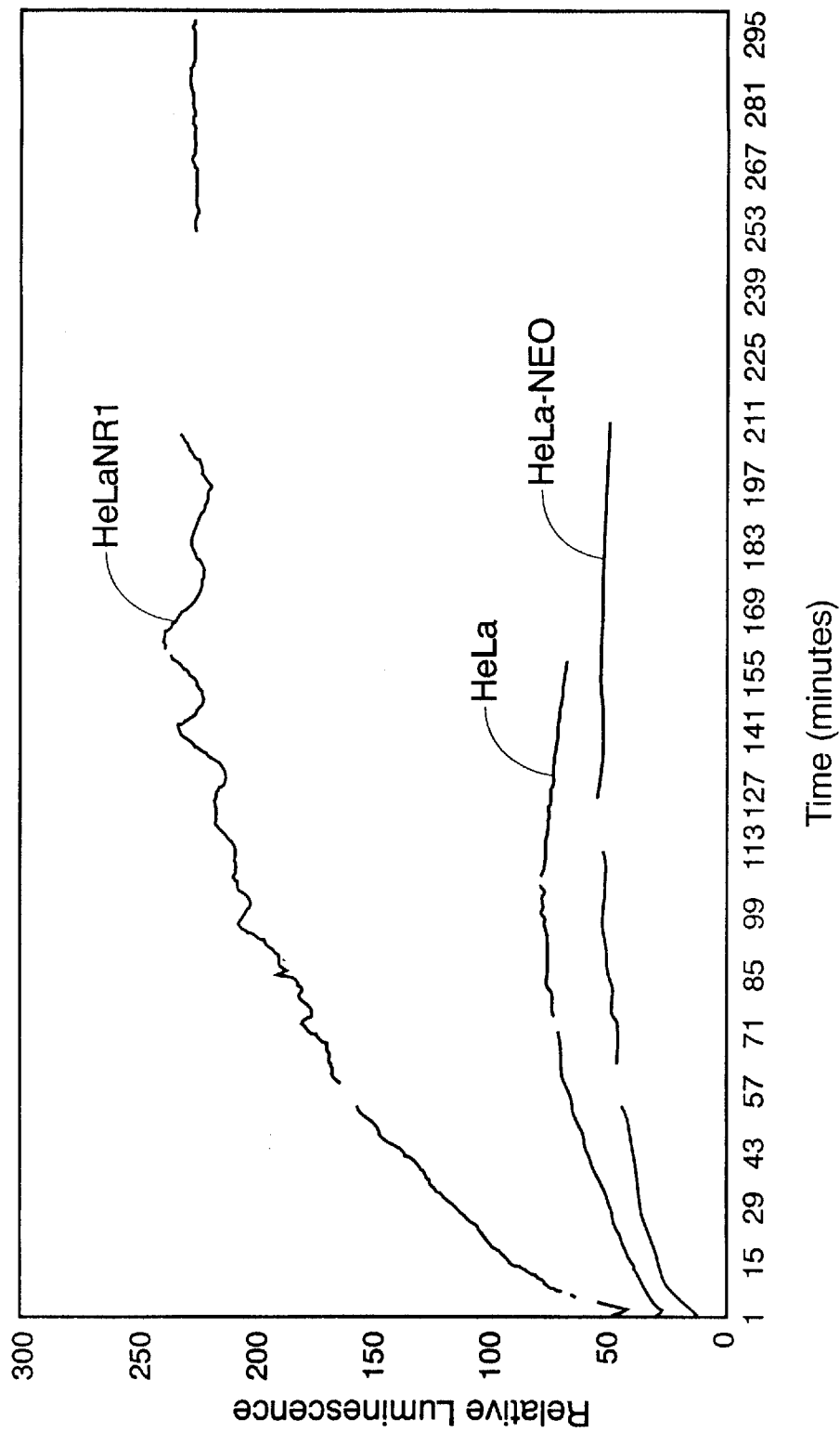
FIG. 1 shows the relative thermochemiluminescence (TCL) of transformed cells, versus non-transformed cells.

The HeLa cell line was obtained from the American Type Culture Collection, Manassas Va.

HeLa cells were transfected with the $pSV_2neoNR10_1$ plasmid using the technique described in Kiel et al, U.S. Pat. No. 5,464,768. The $pSV_2neoNR10_1$ plasmid is the neomycin resistant plasmid $pSV_2neo$ modified by insertion of the 1.1 kb base pair barley nitrate reductase (NR) gene fragment between the EcoR1 sites. As a control, the $pSV_2neo$ plasmid, without the barley nitrate reductase gene fragment, was introduced into this cell line. The transfectants were selected for by using 500 micrograms/ml of the antibiotic Geneticin (neomycin) in the growth medium. An active clone designated HeLaNR1 was isolated in addition to the control plasmid clone. The control clone was designated Hela-NEO. The HeLaNR1 cells were grown in RPMI 1640 medium, without phenol red, containing 12:0.1:0.08 mass ratio per unit volume of potassium nitrate, luminol and 3-amino-L-tyrosine•HCl (3AT), respectively. This medium was designated 2×. 10 U/ml of human gamma-interferon and 5 nanograms/ml of E. coli endotoxin (LPS) were added to some of the media preparations to induce DALM formation. The clone HeLaNR1 was deposited with the American Type Culture Collection Apr. 8, 1998, receiving the ATCC Designation CRL-12510. All restrictions on the availability to the public of the material so deposited will be irrevocably removed upon the granting of a patent. The deposited material will be maintained with all the care necessary to keep it viable and uncontaminated for a period of at least five years after the most recent request for the furnishing of a sample of the deposited cells, and in any case, for a period of at least thirty (30) years after the date of deposit or for the enforceable life of the patent, whichever period is longer. These transfected HeLa cells produce diazoluminomelanin (DALM) intra cellularly when grown in 3AT media, i.e., media containing nitrate, luminol and 3AT.

FIG. 1 shows the normalized thermochemiluminescence responses of parent cells (HeLa), control transfectants (Hela-NEO), and transfectants (HeLaNR1) after 10 days of culture. Thermoluminescence was induced by adding 100 µl 3% hydrogen peroxide and 100 µl 0.3 M sodium carbonate solutions to 50 µl of phosphate buffered saline washed cells (packed cells in 150 µl PBS) and heating the preparation to 45° C., while observing the luminescence in a Turner 20e Luminometer (Mountain View Calif.).

The cell line HeLaNR1 has utility in determining the parameters necessary for functional transfection of human cells with the nitrate reductase gene, the insertion point in human cells of the nitrate reductase gene, the effects of chronic enhanced nitric oxide/nitrite production on human cells, and the potential for sensitizing cancer cells to microwave radiation killing for therapeutic purposes.

Various modifications may be made to the invention as described without departing from the spirit of the invention or the scope of the appended claims.

We claim:
1. The cell line HeLaNR1.

* * * * *